United States Patent
Haag

(10) Patent No.: US 6,277,124 B1
(45) Date of Patent: Aug. 21, 2001

(54) METHOD AND APPARATUS FOR RATCHETING ADJUSTMENT OF BONE SEGMENTS

(75) Inventor: Rene Haag, Berwyn, PA (US)

(73) Assignee: Synthes (USA), Paoli, PA (US)

( * ) Notice: Subject to any disclaimer, the term of this patent is extended or adjusted under 35 U.S.C. 154(b) by 0 days.

(21) Appl. No.: 09/428,330

(22) Filed: Oct. 27, 1999

(51) Int. Cl.$^7$ ................................................ A61B 17/56
(52) U.S. Cl. .................................... 606/105; 606/57
(58) Field of Search ................................ 606/105, 57, 58, 606/71

(56) References Cited

U.S. PATENT DOCUMENTS

| | | |
|---|---|---|
| 268,632 | 12/1882 | Danforth . |
| 3,385,299 | 5/1968 | Le Roy ............................ 128/337 |
| 3,604,414 | * 9/1971 | Borges ............................. 606/105 |
| 3,659,595 | 5/1972 | Haboush .......................... 128/92 |
| 5,672,177 | * 9/1997 | Seldin ............................. 606/105 |
| 5,700,263 | 12/1997 | Schendel ......................... 606/57 |
| 5,807,382 | * 9/1998 | Chin ............................... 606/105 |
| 5,827,286 | 10/1998 | Incavo et al. .................... 606/71 |
| 5,885,283 | * 3/1999 | Gittleman ........................ 606/71 |
| 6,093,189 | * 7/2000 | Sellers ............................ 606/105 |
| 6,182,004 | * 2/2001 | Fearon ............................ 606/105 |

FOREIGN PATENT DOCUMENTS 0923532  4/1982  (RU) .

WO 96/36291  11/1996  (WO) .

* cited by examiner

Primary Examiner—Paul J. Hirsch
(74) Attorney, Agent, or Firm—Pennie & Edmonds LLP

(57) ABSTRACT

The present invention provides an improved orthopedic method and system for incremental adjustment of the bone segments on either side of a bone repair site. The apparatus includes a ratchet assembly which may be subcutaneously implanted, and an adjustment assembly which may be inserted percutaneously for releasable engagement with the adjustment assembly. The ratchet assembly includes a first piece having a tongue with ratcheting serrations, and a second piece having a cavity to receive the tongue and also including ratcheting pawls to engage the serrations. The serrations and the pawl cooperate to act as a uni-directional ratchet; depending on the geometry of the serrations, the ratchet assembly may operate as an incremental distractor or reducer. The adjustment assembly may be a simple threaded shaft which engages with a threaded bore on one of the pieces of the ratchet assembly; in this embodiment as the shaft is rotated, its end will provide a force to the other piece of the ratchet assembly. Alternatively, the adjustment assembly may be a plunger-type device having a sleeve portion which hooks onto one of the pieces of the ratchet assembly and a plunger portion which provides a force to the other piece of the ratchet assembly. The system advantageously allows the adjustment assembly to be removed from the patient when not in use, and provides a low-profile design for the adjustment assembly (reducer, distractor, etc.) which allows for convenient subcutaneous implantation. The adjustment assembly may be constructed in whole or part from bio-absorbable materials.

27 Claims, 5 Drawing Sheets

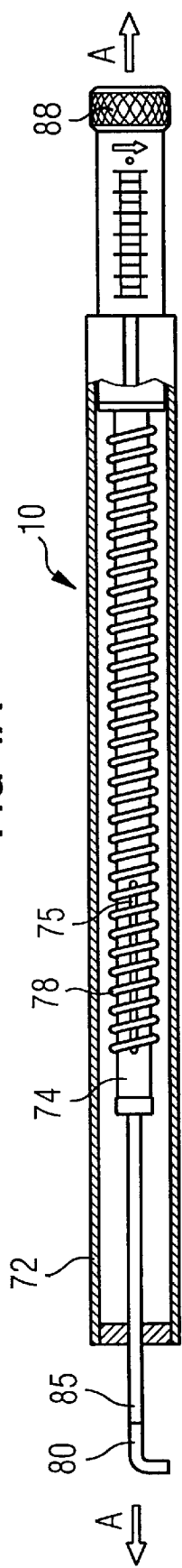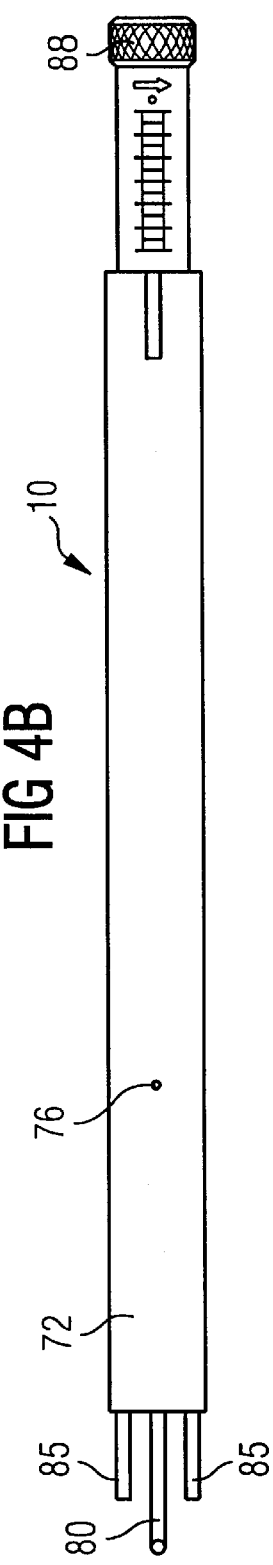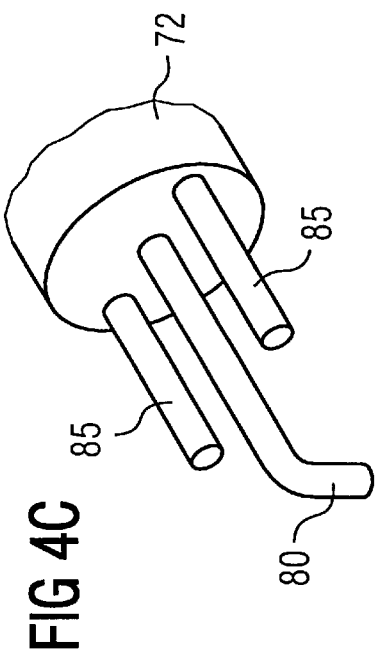

METHOD AND APPARATUS FOR RATCHETING ADJUSTMENT OF BONE SEGMENTS

TECHNICAL FIELD

The present invention relates to an orthopedic system and, more particularly, to an improved orthopedic system for controlled ratcheting adjustment of the separation of bone segments on either side of a bone repair site.

BACKGROUND OF THE INVENTION

A variety of orthopedic devices for controlled relative adjustment of the separation and orientation of bone segments are known in the art. For example, distraction devices (commonly referred to as distractors) are known. Typically, distractors are used to perform distraction osteogenesis. This procedure was perfected by the Russian orthopedic doctor, Gavriel Ilizarov. A typical procedure of this type involves at most an osteotomy completely separating the bone into two segments, or at least an incision of the cortical portion of the bone. Then, the bone segments on either side of the bone repair site may be incrementally separated. As used herein "bone repair site" refers to any bone region which is desired to be treated using the orthopedic system and which is bounded on opposing sides by relatively healthy bone regions to which orthopedic devices can be secured. The bone repair site will often be an osteotomy or a fracture. The incremental separation of the bone segments allows new bone to form in the osteotomy void; this is variously referred to as osteosynthesis or osteogenesis, among other terms. This incremental "distraction phase" is followed by a "consolidation phase," during which the distractor is held fixed, and the new bone growth gains strength. Following the consolidation phase, the distractor is removed from the patient. In addition to distractors, it is also known to provide reduction devices, or "reducers," for controllably and gradually bringing separated bone segments together.

The design of the early reducers and distractors, which used bone pins and screws to attach the externally-mounted devices to the bone, are known to have certain problems. For example, numerous pins are needed to attach a single device; at a minimum, two pins are required (one for the part of the device associated with each bone segment), but typically, many more are used. Each pin necessitates a transcutaneous incision, thus multiplying the risk of infection to the patient. Furthermore, a pin clamp or coupling is required to join the fixation/distraction mechanism to the pins, and the design and operation of these couplings are complicated by the difficulty encountered in aligning the pins accurately when they are inserted into the bone. Additionally, because the pins extend in a generally perpendicular direction from the insertion site, the resultant overall device sticks out quite far from the patient's body (i.e., the device has a high profile), and the device is unsightly. A high-profile device also is more subject to bumps and snags than one maintained tight to the patient's body. Further, aesthetic considerations are important because a high-profile device may be rejected by prospective patients, especially children.

Accordingly, more recent devices have been designed not to use transcutaneous pins for attachment to the bone, but rather to use more low-profile bone anchors, such as plates with screw holes, as part of a low-profile overall device. This improved prior art is exemplified by U.S. Pat. No. 5,364,396 to Robinson et al., which discloses an implantable bone distraction device which includes low profile blocks for attachment to osteotomically separated bone sections. As disclosed, the entire device can be implanted subcutaneously, except for a transcutaneous actuator assembly which is linked to the implanted distraction assembly, and allows adjustment of the distraction increment from outside the patient's body. The difficulty with this device is that it requires the subcutaneous implantation of a rather large mechanism, with the result that it is difficult to hide the presence of the implant.

U.S. Pat. No. 3,604,414 to Borges also discloses an implantable bone reduction device designed to be adjusted using an external apparatus. The reduction plate is of two-piece construction, with the plates incorporating opposing toothed sections. The toothed sections prevent relative movement of the plates in the direction of fracture separation, but allow movement in the direction of fracture reduction. A tool for moving the plates toward each other is provided to facilitate engagement of the plates after they have been attached to the opposing segments of bone. The difficulty with this device is that it requires the osteotomy site to be fully uncovered each time an adjustment is made, since the adjustment tool resembles a caliper, and engages the opposing plates from above, and in a perpendicular orientation, which requires full access to the face of each plate. Such an invasive surgery increases the likelihood for infection and scarring.

U.S. Pat. No. 5,672,167 to Seldin and U.S. Pat. No. 5,827,286 to Incavo et. al. disclose implantable bone distraction devices designed to be adjusted without first reopening the osteotomy site. Both disclose devices comprising two plates, each of which is attached to a bone segment, and which plates engage one another. The devices are designed to operate in a ratcheting manner in response to the extracorporeal application of force. These ratchets allow relative movement of the plates in one direction along the system axis, but not the reverse. The Seldin device is actuated by the application of force to a pre-tensioned ratchet arm incorporated into the first plate. This ratchet arm contacts a corresponding ratchet pawl on the second plate and forces the two plates apart, thereby achieving distraction of the attached bone segments. The ratchets then prevent the plates from assuming their previous position. The difficulty with the Seldin device is that it provides an imprecise and inaccurate means of measuring bone distraction. The Seldin device has a further disadvantage of requiring that the external actuating force be applied perpendicular to the bone axis. This perpendicular force may tend to cause increased patient discomfort. Additionally, the Seldin device requires the actuating force be applied at or near the suture location, which also may result in increased discomfort, suture healing problems, or scarring. With the Incavo device, bone lengthening is achieved through the use of an external extension brace which is manipulated to apply force directly to the patient's limb. The Incavo device extends in response to this manual distraction, and its ratchet arrangement prevents it and the respective bone segments from returning to their prior position. The difficulty with the Incavo device is that it requires the use of large external alignment apparatus, and may not be adaptable to small bone distractions such as in maxillofacial applications.

Accordingly, there is a need in the art to provide a low profile, aesthetically pleasing, subcutaneous distractor that minimizes the total volume of implant installed, while providing maximum flexibility, precision, and accuracy in adjusting incrementally the distance between separated bone halves.

SUMMARY OF THE INVENTION

The present invention addresses the need in the art by providing an orthopedic adjustment system consisting of a small implantable ratchet assembly, the halves of which are attachable to opposing segments of bone, and which are incrementally adjustable in one direction along the system axis but not the other. The manipulation of the ratchet assembly, and thus its incremental distraction or reduction, is achieved through the temporary attachment of an elongated percutaneous actuation assembly inserted through a small opening in the patient's skin, the size of which hole is substantially smaller than the ratchet pieces. The adjustment assembly may be either of flexible or rigid construction, and may comprise either a sleeve and plunger or a solid advancing screw configuration. The ratchet assembly is attached to the associated bone segments with bone screws, and the assembly as well as the bone screws may be made of a bio-absorbable material to eliminate the need for post-procedure removal. This adjustment system can operate as either a reducer or a distractor, allowing precise and accurate control of bone position, while providing a low profile implanted device that aesthetically is more acceptable to a patient, and which reduces overall chance for infection at the incision site.

Specifically, the present invention provides a ratcheting orthopedic adjustment system comprising a ratcheting assembly, having a system axis, which maybe aligned in the direction of the orthopedic adjustment. The assembly permits incremental relative movement in a first direction along the system axis but not in the opposite direction. The ratcheting assembly comprises a first ratchet piece for attachment to a first bone segment, and a second ratchet piece for attachment to a second bone segment, and an elongated percutaneous adjustment assembly. The ratcheting assembly may comprise, for example, a reducer (in which case the first direction represents a decrease in the separation between the ratchet pieces, so as to facilitate consolidation of the bone segments) or a distractor (in which case the first direction represents an increase in the separation between the ratchet pieces, so as to permit osteosynthesis in the bone repair region between the bone segments).

The adjustment assembly is releasably engageable with the ratcheting assembly. The adjustment assembly has a portion which is insertable through an opening in the patient's skin substantially smaller than the dimension of the ratcheting assembly, and a portion which remains outside the patient's body and is for manipulation. After the ratcheting assembly is subcutaneously implanted, the adjustment assembly may be inserted through the opening, releasably engaged with the ratcheting assembly, manipulated to achieve an incremental relative movement of the first and second ratchet pieces in the first direction, disengaged from the ratcheting assembly, and finally may be removed from the opening.

The first ratchet piece comprises a tongue, a first bone-anchoring portion, and a first interaction portion. The first ratchet piece is substantially planar, having a top surface, a bottom surface, and two side surfaces, the side surfaces being provided with ratchet serrations. The second ratchet piece comprises a housing, a second bone-anchoring portion, and a second interaction portion. The housing has a cavity shaped to accept the insertion of the tongue, and also has one or more ratchet pawls for engagement with the ratchet serrations. The bone-anchoring portions of the ratchet pieces may be screw holes which accept bone screws to attach the ratchet pieces to the associated bone segments.

The present invention also provides that the ratcheting assembly may be made in full or part from a bio-absorbable material. In this embodiment, if screws are used for insertion through the screw holes to attach the ratchet pieces to the associated bone segments, these bone screws may be made of a bio-absorbable material which takes at least as long to be absorbed by the patient as does the part of the ratcheting assembly which is made of bio-absorbable material.

The present invention also provides an adjustment assembly comprising an elongated sleeve for engaging one of the ratchet pieces, an elongated plunger for engaging the other ratchet piece (the plunger being slidingly accepted by the sleeve), and an adjustment assembly axis generally defined by the longitudinal centerline of the adjustment assembly.

When the sleeve and plunger of the adjustment assembly are releasably engaged with their respective ratchet pieces, manipulation of the adjustment assembly (by adjusting the relative positions along the adjustment assembly axis of the sleeve and plunger) achieves a modification of the relative position of the first and second ratchet pieces in a first direction along the system axis. The mechanical interaction of the ratchet serrations of the first ratchet piece with the ratchet pawls of the second ratchet piece permit the incremental relative movement in the first direction, while mechanically preventing relative movement in a second direction opposed to the first direction.

The present invention also provides that the sleeve may be provided with a hole transverse to the longitudinal bore, and the plunger may be provided with a distal pushing end, an intermediate section having a longitudinal slot, and a proximal pushing end. With the plunger positioned in the bore of the sleeve, a pin may be placed through the transverse hole in the sleeve and also through the slot in the plunger. The pin will then mechanically limit the relative displacement of the sleeve and the plunger along the longitudinal adjustment axis. The adjustment assembly may further be provided with a biasing spring located so as to mechanically bias the relative displacement of the sleeve and the plunger along the longitudinal axis.

The present invention also provides that one of the interaction portions may comprise an indentation or hole in the respective ratchet piece. In this case, the corresponding engagement portion of the adjustment assembly may comprise a hook-shaped portion shaped to releasably mechanically engage with that indentation or hole.

The adjustment assembly may comprise a ratchet engagement end for engaging one of the ratchet pieces, a ratchet engagement portion for engaging the other ratchet piece, and an adjustment assembly axis generally defined by the longitudinal centerline of the adjustment assembly. The ratchet engagement portion is threadably accepted by the respective ratchet piece. The interaction portion of the respective ratchet piece comprises an internally threaded bore which threadably accepts the external threading on the engagement portion of the activation assembly. When the threads of the ratchet engagement portion are engaged with the respective ratchet piece, manipulation of the adjustment assembly achieves a modification of the relative position of the first and second ratchet pieces in the first direction. The interaction portion which is not the internally threaded bore may comprise a raised portion shaped to mechanically engage the ratchet engagement end of the adjustment assembly.

The adjustment assembly may also comprise an elongated sleeve having a longitudinal through bore, the sleeve being capable of engaging one of the ratchet pieces, and an elongated plunger, slidingly accepted by the sleeve, for engaging the other ratchet piece. When the sleeve and plunger are engaged with their respective ratchet pieces, manipulation of the adjustment assembly by adjusting the relative positions, along the adjustment assembly axis, of the sleeve and plunger, modifies the relative position of the first and second ratchet pieces along the system axis.

The adjustment assembly may comprise an activation screw and an activation tool. The activation screw includes: a substantially cylindrical exterior surface, a tool engagement end, a ratchet engagement end for engaging one of the ratchet pieces, a ratchet engagement portion for engaging the other ratchet piece (the ratchet engagement portion comprising an external threading along a portion of the activation screw), and a longitudinal screw axis generally defined by the longitudinal centerline of the activation screw. One of the ratchet pieces is provided with an internally threaded bore which threadably accepts the external threading on the engagement portion of the activation screw. In this embodiment, the activation screw may be rotated about the longitudinal screw axis by engaging the activation tool with the tool engagement end of the activation screw, such that the interaction of the external threading of the ratchet engagement portion and the internally threaded bore of the associated ratchet piece results in a modification of the relative position of the activation screw and the associated ratchet piece along the longitudinal screw axis. The end result is that the ratchet engagement end of the activation screw transmits a force to the other ratchet piece, resulting in a modification of the relative positions of the first and second ratchet pieces along the system axis.

The present invention also provides that the adjustment assembly may be substantially rigid, in which case the adjustment assembly axis follows a fixed line. Alternatively, the adjustment assembly may be flexible, permitting shaping of the adjustment assembly such that the line followed by the adjustment assembly axis can be varied.

The present invention also provides a method for treating a bone repair site in a patient, using an adjustment assembly comprising a longitudinal axis, a first adjustment portion, and a second adjustment portion, wherein the first and second adjustment portions are slidingly engaged to permit controlled relative displacement along the longitudinal axis. The method begins with the steps of subcutaneously implanting a first ratchet piece on the patient's bone on one side of the bone repair site and subcutaneously implanting a second ratchet piece on the patient's bone on the other side of the bone repair site. Then method next involves percutaneously inserting the adjustment assembly through an incision in the patient's skin (the incision being substantially smaller than the ratchet pieces); releasably engaging the adjustment assembly with the first and second ratchet pieces; displacing the first and second adjustment portions relative to each other, so as to result in an incremental modification of the distance separating the first and second ratchet pieces; disengaging the adjustment assembly from the ratchet pieces; and removing the adjustment assembly from the patient. The steps involving the adjustment assembly may be repeated as desired or necessary to treat the bone repair site. This method may also include fabricating part or all of the ratchet assembly, and the bone screws used to attach the assembly to the opposing bone segments, of a bioabsorbable material.

BRIEF DESCRIPTION OF THE DRAWINGS

The features and advantages of the present invention will become more readily apparent from the following detailed description of the invention in which like elements are labeled similarly and in which:

FIGS. 4A, 4B, and 4C are a side, cutaway, and perspective end view, respectively, of the first embodiment of the actuation assembly of a system as illustrated in FIG. 1;

DETAILED DESCRIPTION OF THE PREFERRED EMBODIMENTS

The orthopedic device of the present invention is discussed herein with reference to a preferred embodiment adapted to be used in a linear distraction of an osteotomically separated bone. It is to be understood that the invention is not limited to distraction, but rather finds general application for use with either orthopedic distraction or reduction devices. Furthermore, it will be clear that the invention finds applicability for use in any circumstance in which it is desired to adjust or control the separation of bone segments on either side of a bone repair site.

Figure 1:
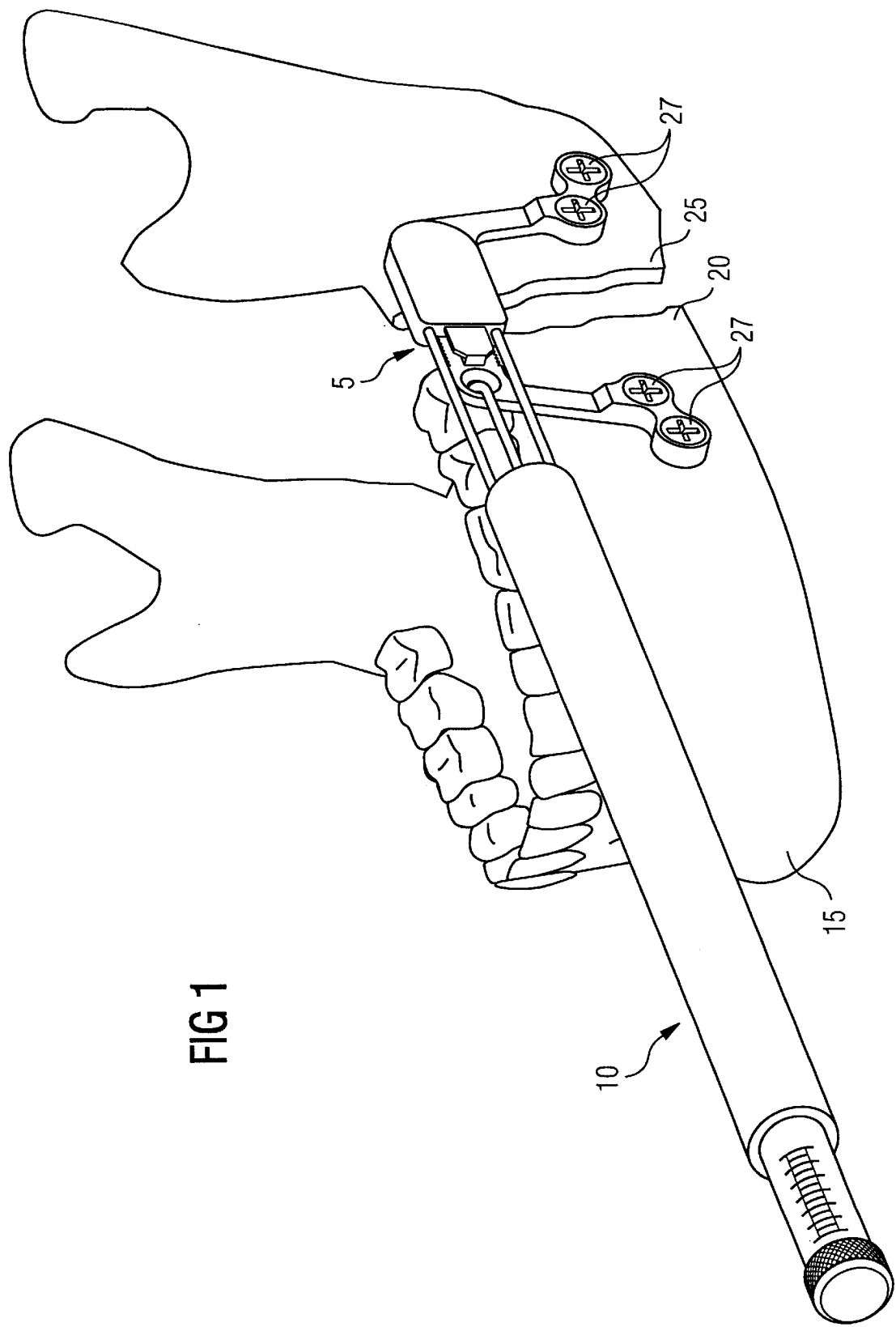
FIG. 1 is a perspective view of a first embodiment of the ratcheting orthopedic device of the present invention, illustrating the orthopedic device attached to bone segments on either side of a bone repair site.

Referring more particularly to the drawings, FIG. 1 shows an osteotomic distraction system. As shown in FIG. 1, the distraction system comprises a low profile ratchet assembly 5 and actuation assembly 10 which allow incremental adjustment of the ratchet halves 30, 60 (shown in FIGS. 2A, 2B, 3A, 3B, 5, and 8) which are attached to opposing segments 20, 25 of an osteotomically separated bone 15.

At installation the ratchet assembly 5, comprising the first 30 and second 60 ratchet halves, is assembled such that the ratchet serrations or teeth 35 provided on the side surfaces of tongue 33 of the first ratchet half 30 fit within the cavity of the housing 65 and engage the ratchet pawls 70 (shown in FIGS. 3A and 3B) of the second ratchet half 60. The ratchet assembly 5 is installed subcutaneously, the first and second ratchet halves being anchored to the bone by way of bone-anchoring portions. For example, bone screws 27 may be accepted by screw holes 28 in each of the ratchet halves, to anchor the assembly to pre-drilled bone surfaces on opposing bone segments 20, 25.

After the ratchet assembly 5 is installed, the actuation assembly 10 is inserted percutaneously through an incision in the patient's skin. Based on the small cross-sectional area of the actuation assembly relative to the ratchet halves, the incision may be substantially smaller than the size of the ratcheting distraction assembly 5. The actuation assembly 10 subcutaneously engages the ratchet assembly 5 and one or more incremental steps in the distraction procedure, corresponding to one or more ratchet increments, are performed with no need for additional or larger incisions. The actuation assembly is then removed. The actuation assembly can be repeatedly inserted and removed as desired to perform the distraction. The combination of low-profile ratchet assembly 5 and removable actuation assembly 10 in this way minimizes the aesthetic impact of present distraction devices implanted beneath the skin. Patient distress at receiving the implant is correspondingly reduced.

Figure 8:
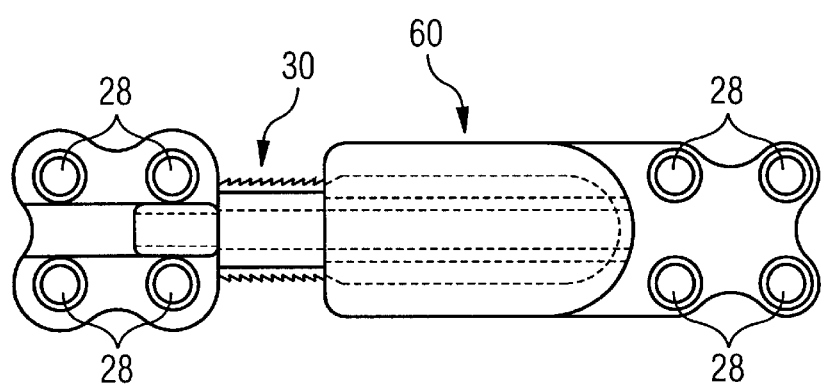
FIG. 8 is a perspective view of a third embodiment of the ratchet assembly of the present invention.

The ratchet assembly 5 is a low-profile design, and as such the design of the ratchet arms 40 and the placement of the screw holes 28 which connect the interaction portions 30, 60 of the ratchet assembly 5 to the associated bone segments may be varied to ensure ease of installation and actuation for the specific implantation location. For example, FIG. 8 shows another possible embodiment, with the placement and number of screw holes 28 varied, as compared with FIGS. 2A, 2B, 3A, 3B, and 5, for a different bone site application, but many others are possible as will be obvious to one of ordinary skill in the art.

The actuation assembly, as shown in FIGS. 4A, 4B, 4C, 6A, 6B, 7A and 7B, can be either of a plunger type or of a solid screw type, and can be either rigid or flexible.

The actuation assembly of the plunger type allows an operator to adjust the distance between ratchet halves, and so the distance between bone halves, by depressing knurled knob 88 (shown in FIGS. 4A and 4B) on the distal pushing end of the assembly, forcing a displacement of the plunger relative to the sleeve along the adjustment assembly axis A—A. This displacement results in a force being applied to the interaction portions of the first and second ratchet halves, causing a corresponding relative displacement of the first and second ratchet halves.

Figure 2A:
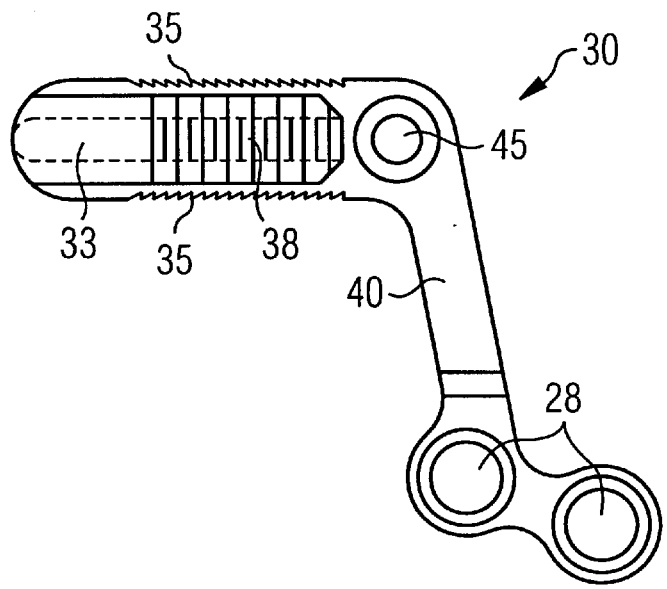
FIGS. 2A and 2B are side and end views, respectively, of the ratchet tongue half of a system as illustrated in FIG. 1.
Figure 2B:
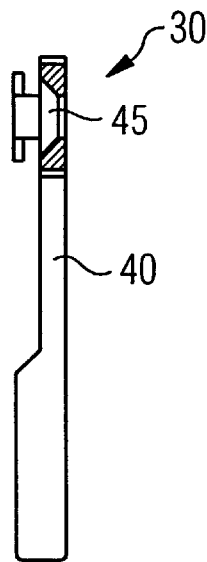
Figure 3A:
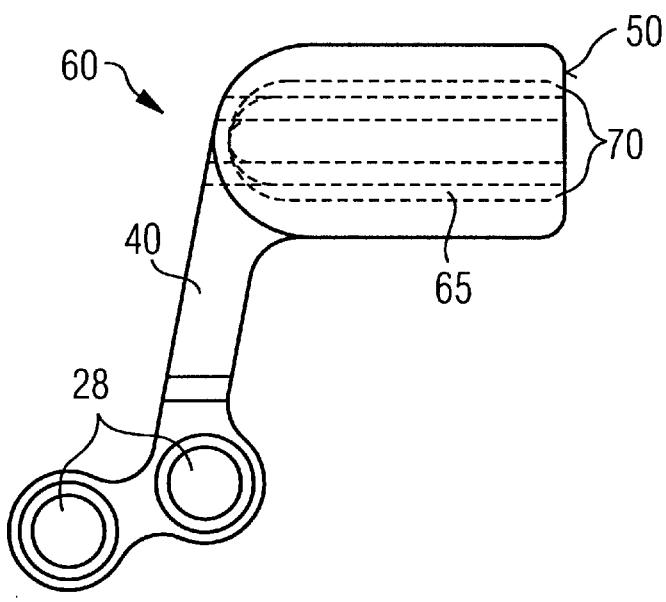
FIGS. 3A and 3B are side and end views, respectively, of the ratchet housing half of a system as illustrated in FIG. 1.
Figure 3B:
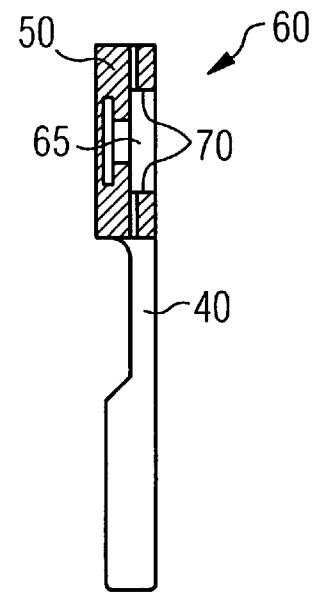

In a preferred embodiment, the actuation assembly of the plunger type incorporates an engagement portion, in the form of a hook 80 fixed on the end of hollow sleeve portion 72, which is received in an interaction portion, in the form of an indentation or hole 45, in the first ratchet half 30 (shown in FIGS. 2A and 2B). It further includes a slideable plunger portion 74, having at its front end, or proximal pushing end, an engagement portion in the form of prongs 85 which contact an interaction portion, in the form of the end face of 50 of the housing 65, of the second ratchet half 60 (as shown in FIGS. 3A and 3B).

As shown in FIG. 4A, an intermediate section of the plunger portion 74 may have a longitudinal slot 75, interacting with a pin 76 which is affixed in a radial or transverse hole in the sleeve portion. The interaction of this pin with the slot 75 in the plunger portion provides a mechanical stop for the relative motion of the plunger and sleeve portions. Also, the activation assembly may be provided with a coil spring 78 which provides a biasing force which provides some resistance to activation of the device.

Figure 5:
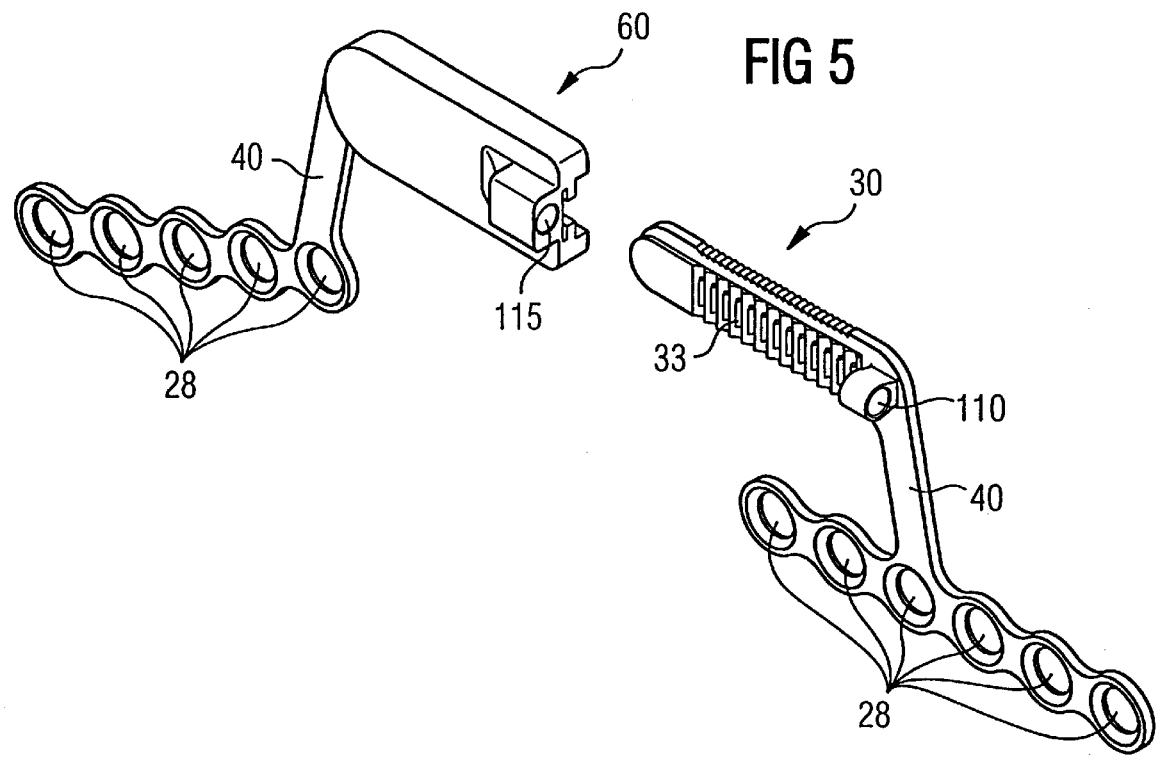
FIG. 5 is a perspective view of a second embodiment of the ratchet assembly of the present invention.
Figure 6A:
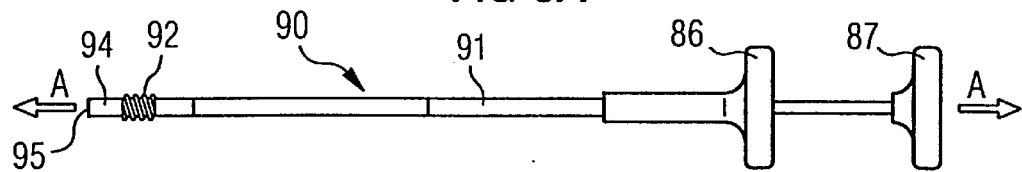
FIGS. 6A and 6B are perspective views of a second and a third embodiment of the actuator assembly of the present invention.
Figure 6B:
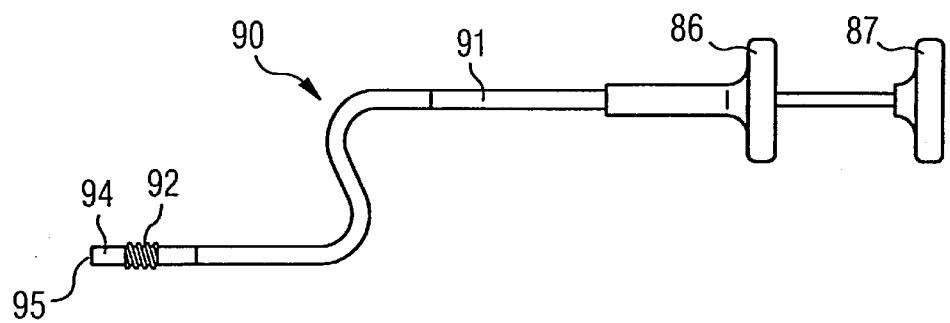

FIGS. 6A and 6B illustrate an alternate embodiment of the plunger type actuation assembly 90 that incorporates a hollow outer-sleeve portion 91 terminating in a ratchet engagement portion in the form of an externally threaded portion 92. This threaded portion 92 is threadably received in an interacting portion in the form of an internally threaded bore 110 in the first ratchet half 100 (shown in FIG. 5). The assembly also includes a slideable plunger portion 94 slideably accepted in the sleeve portion, the plunger having a ratchet engagement end 95 which contacts an interaction portion in the form of a raised block portion 115 on the second ratchet half 105 (shown in FIG. 5). By squeezing handgrip portions 86 and 87 together, in the manner of the well-known cable shutter release for photographic cameras, the slideable segment 94 is displaced axially with respect to the outer sleeve portion 91.

Figure 7A:
FIGS. 7A and 7B are perspective views of a fourth and a fifth embodiment of the actuator assembly of the present invention.
Figure 7B:
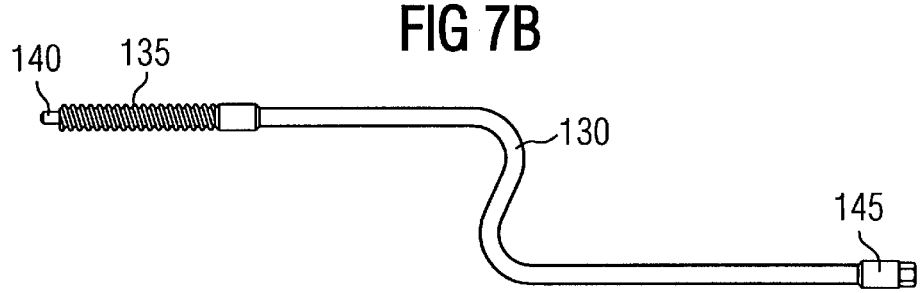

FIGS. 7A and 7B illustrate another alternative embodiment of the actuation assembly, having a solid screw 130 incorporating an external threading 135. The threading can be along an intermediate portion of the length of the screw (as shown), or along its full length. The threading is threadably receivable in an internally threaded bore 110 in the first ratchet half 30 (shown in FIG. 5), and the blunt distal end 140 of the screw directly contacts a raised block portion 115 on the second ratchet half 60 (shown in FIG. 5). The actuation assembly of the solid screw type 130 allows an operator to adjust the distance between ratchet halves 30, 60, and so the distance between bone segments 20 and 25, by twisting the screw proximal end 145, resulting in an axial motion of the screw as it rotates in the bore 110 of the first ratchet piece 30, and causing a contact of the blunt distal end 140 (the engagement end) of the screw with the raised block portion 115 (the interaction portion) of the second ratchet half 60, which in turn causes a relative displacement of the first and second ratchet halves. The proximal end may be configured to engage with a tool, such as a screwdriver or wrench, which may be used to rotate the screw.

As shown in FIGS. 6A, 6B, 7A and 7B, the actuation assembly of either the plunger 90 or solid screw 130 type can be either flexible or rigid or a combination of flexible and rigid. If rigid, the shape of the actuation assembly is fixed, and the adjustment assembly axis follows a fixed line. If flexible, the shape of the actuation assembly is variable, permitting shaping of the adjustment assembly such that the line followed by the adjustment assembly axis is variable. It is envisioned that a fully or partially flexible assembly (see FIGS. 6B and 7B) will provide ease and comfort of distraction which might not be possible with a completely rigid assembly. This is a matter of personal preference for the patient or physician and does not eliminate the advantage of utilizing a completely rigid actuation assembly.

In an alternate embodiment of the ratchet assembly 5, and as a way of reducing patient trauma associated with post-procedural removal of the ratchet assembly, some or all of the ratchet assembly can be fabricated of a bio-absorbable material such as a resorbable polyester. The selection of a particular bio-absorbable material is dictated by the need to maintain ratchet assembly integrity throughout the full term of the distraction, reduction, or healing procedure.

Similarly the bone screws utilized to secure the ratchet assembly to the opposing bone segments 20, 25 can be fabricated of bio-absorbable material. Where bio-absorbable bone screws are utilized with a bio-absorbable ratchet assembly, selection of a particular bone screw material should be such that it lasts at least as long as that selected for the bio-absorbable ratchet assembly.

In an embodiment of the present invention suitable for maxillofacial applications, such as illustrated in FIGS. 1 and 5, the ratchet assembly 5 is designed with elongated ratchet arms 40, such that the interaction portions of the device are offset from the bone-anchoring portions. This allows the device to be installed in an intra-oral position, such that it sits between the patient's cheek and gum. Such an application has the benefit of reducing the number and size of the incisions required for installation of the ratchet assembly, as well as further reducing aesthetic disruption since there is no need to maintain an incision for insertion of the adjustment assembly. In addition, an intra-oral installation would allow the operator to measure directly the total length of distraction since the ratchet assembly would be directly observable inside the patient's mouth. Usage in this manner can be further aided by the provision of a scale 38 (as shown in FIGS. 2A and 5) directly onto the outside visible portion of the ratchet half or halves. This permits precise distraction without the need for external measurement devices.

It should be emphasized that the above described embodiments of the present invention are merely exemplary, adapted for specific applications in the human skeletal system. The modifications appropriate for other applications may readily be realized by those who are skilled in the art and who have been equipped with the understanding of the structure and operation of the present invention as set forth in the above description.

For example, the particular distractor system shown in FIGS. 1 through 8 could be used, with modifications obvious to those of skill in the art, in orthopedic reduction procedures simply by changing the sense of the slopes of the ratchet teeth and pawls, without departing from the spirit or scope of the present invention. Accordingly, it should be understood that the embodiment herein is merely illustrative of the principles of the invention. Various other modifications may be made by those skilled in the art which will embody the principles of the invention and fall within the spirit and the scope thereof.

What is claimed is:

1. A ratcheting orthopedic adjustment system comprising:
   (a) a ratcheting assembly, having a system axis, for incremental relative movement in a first direction along the system axis but not in the opposite direction, the ratcheting assembly comprising a first ratchet piece for attachment to a first bone segment, and a second ratchet piece for attachment to a second bone segment; and
   (b) an elongated percutaneous adjustment assembly having a portion which is insertable through an opening in the patient's skin substantially smaller than the dimension of the ratcheting assembly and is releasably engageable with the ratcheting assembly, and a portion which remains outside the patient's body and is for manipulation;
   wherein after the ratcheting assembly is subcutaneously implanted, the adjustment assembly may be inserted through the opening, releasably engaged with the ratcheting assembly, manipulated to achieve an incremental relative movement of the first and second ratchet pieces in the first direction, disengaged from the ratcheting assembly and removed from the opening.

2. The ratcheting orthopedic adjustment system of claim 1 wherein
   (a) the system axis is aligned in the direction of the orthopedic adjustment;
   (b) the first ratchet piece comprises a tongue, a first bone-anchoring portion, and a first interaction portion, the first ratchet piece being substantially planar, having a top surface, a bottom surface, and two side surfaces, the side surfaces being provided with ratchet serrations;
   (c) the second ratchet piece comprises a housing, a second bone-anchoring portion, and a second interaction portion, the housing having a cavity shaped to accept the insertion of the tongue and further having one or more ratchet pawls for engagement with the ratchet serrations;
   (d) the adjustment assembly further comprises an elongated sleeve for engaging one of the ratchet pieces; an elongated plunger for engaging the other ratchet piece, the plunger being slidingly accepted by the sleeve; and an adjustment assembly axis generally defined by the longitudinal centerline of the adjustment assembly;
   whereby when the sleeve and plunger of the adjustment assembly are releasably engaged with the respective ratchet pieces, manipulation of the adjustment assembly by adjusting the relative positions along the adjustment assembly axis of the sleeve and plunger achieves a modification of the relative position of the first and second ratchet pieces in a first direction along the system axis, the interaction of the ratchet serrations of the first ratchet piece with the ratchet pawls of the second ratchet piece allowing the incremental relative movement of the first and second ratchet pieces in the first direction while mechanically preventing relative movement of the first and second ratchet pieces in a second direction opposed to the first direction.

3. The system of claim 2 wherein one of the interaction portions comprises an indentation or hole in the respective ratchet piece, and the corresponding engagement portion of the adjustment assembly comprises a hook-shaped portion shaped to releasably mechanically engage with the indentation or hole.

4. The system of claim 2 wherein
   the sleeve further comprises a hole transverse to the longitudinal bore; the plunger further comprises a distal pushing end, an intermediate section having a longitudinal slot, and a proximal pushing end; and the adjustment assembly further comprises a biasing spring and a pin;
   such that when the plunger is positioned in the bore of the sleeve, the pin may be placed through the transverse hole in the sleeve and also through the slot in the plunger, the pin thereby mechanically limiting the relative displacement of the sleeve and the plunger along the longitudinal adjustment axis, and the spring is located so as to mechanically bias the relative displacement of the sleeve and the plunger along the longitudinal axis.

5. The system of claim 2 wherein the adjustment assembly is substantially rigid, and the adjustment assembly axis follows a fixed line.

6. The system of claim 2 wherein the adjustment assembly is flexible, permitting shaping of the adjustment assembly such that the line followed by the adjustment assembly axis is variable.

7. The system of claim 2 wherein the bone-anchoring portions comprise screw holes, and which system further comprises bone screws for insertion through the screw holes to attach the ratchet pieces to the associated bone segments.

8. The system of claim 2 wherein at least part of the ratcheting assembly is made of a bio-absorbable material.

9. The system of claim 8 wherein the bone-anchoring portions comprise screw holes, and which system further comprises bone screws for insertion through the screw holes to attach the ratchet pieces to the associated bone segments, the bone screws made of a bio-absorbable material which takes at least as long to be absorbed by the patient as does the part of the ratcheting assembly which is made of bio-absorbable material.

10. The system of claim 2 wherein the ratcheting assembly is a reducer, and the first direction represents a decrease in the separation between the ratchet pieces.

11. The system of claim 2 wherein the ratcheting assembly is a distractor, and the first direction represents an increase in the separation between the ratchet pieces.

12. The ratcheting orthopedic adjustment system of claim 1 wherein
   (a) the system axis is aligned in the direction of the orthopedic adjustment;
   (b) the first ratchet piece comprises a tongue, a first bone-anchoring portion, and a first interaction portion, the first ratchet piece being substantially planar, having a top surface, a bottom surface, and two side surfaces, the side surfaces being provided with ratchet serrations;
   (c) the second ratchet piece comprises a housing, a second bone-anchoring portion, and a second interaction portion, the housing having a cavity shaped to accept the insertion of the tongue and further having one or more ratchet pawls for engagement with the ratchet serrations;

(d) the adjustment assembly further comprises a ratchet engagement end for engaging one of the ratchet pieces; a ratchet engagement portion for engaging the other ratchet piece, the ratchet engagement portion being threadably accepted by the respective ratchet piece; and an adjustment assembly axis generally defined by the longitudinal centerline of the adjustment assembly;

wherein the interaction portion of the respective ratchet piece comprises an internally threaded bore which threadably accepts the external threading on the engagement portion of the activation assembly, and wherein further when the tongue is positioned within the cavity, the ratchet serrations of the first ratchet piece engage with the one or more ratchet pawls of the second ratchet piece to allow incremental relative movement of the first and second ratchet pieces in a first direction along the system axis, while mechanically preventing relative movement of the first and second ratchet pieces in a second direction opposed to the first direction, and whereby when the threads of the ratchet engagement portion are engaged with the respective ratchet piece, manipulation of the adjustment assembly achieves a modification of the relative position of the first and second ratchet pieces in the first direction.

13. The system of claim 12 wherein the interaction portion which is not the internally threaded bore comprises a raised portion shaped to mechanically engage the ratchet engagement end of the adjustment assembly.

14. The system of claim 12 wherein the adjustment assembly comprises:

an elongated sleeve having a longitudinal through bore, and capable of engaging one of the ratchet pieces; an elongated plunger for engaging the other ratchet piece, the plunger being slidingly accepted by the sleeve; and an adjustment assembly axis generally defined by the longitudinal centerline of the adjustment assembly;

whereby when the sleeve and plunger of the adjustment assembly are engaged with the respective ratchet pieces, manipulation of the adjustment assembly by adjusting the relative positions, along the adjustment assembly axis, of the sleeve and plunger, modifies the relative position of the first and second ratchet pieces along the system axis.

15. The system of claim 14 wherein the adjustment assembly is substantially rigid, and the adjustment assembly axis follows a fixed line.

16. The system of claim 14 wherein the adjustment assembly is flexible, permitting shaping of the adjustment assembly such that the line followed by the adjustment assembly axis is variable.

17. The system of claim 12 wherein the adjustment assembly comprises an activation screw and an activation tool, the activation screw comprising:

(a) a substantially cylindrical exterior surface;

(b) a tool engagement end;

(c) a ratchet engagement end for engaging one of the ratchet pieces;

(d) a ratchet engagement portion for engaging the other ratchet piece, the ratchet engagement portion comprising an external threading along a portion of the activation screw; and (e) a longitudinal screw axis generally defined by the longitudinal centerline of the activation screw;

and wherein one of the ratchet pieces further comprises an internally threaded bore which threadably accepts the external threading on the engagement portion of the activation screw, wherein the activation screw may be rotated about the longitudinal screw axis by engaging the activation tool with the tool engagement end of the activation screw, such that the interaction of the external threading of the ratchet engagement portion and the internally threaded bore of the associated ratchet piece results in a modification of the relative position of the activation screw and the associated ratchet piece along the longitudinal screw axis, such that the ratchet engagement end of the activation screw transmits a force to the other ratchet piece, resulting in a modification of the relative positions of the first and second ratchet pieces along the system axis.

18. The system of claim 17 wherein the activation screw is substantially rigid, and the adjustment assembly axis follows a fixed line.

19. The system of claim 17 wherein the activation screw is flexible, permitting shaping of the adjustment assembly such that the line followed by the adjustment assembly axis is variable.

20. The system of claim 17 wherein the bone-anchoring portions comprise screw holes, and which system further comprises bone screws for insertion through the screw holes to attach the ratchet pieces to the associated bone segments.

21. The system of claim 12 wherein at least part of the ratcheting assembly is made of a bio-absorbable material.

22. The system of claim 21 wherein the bone-anchoring portions comprise screw holes, and which system further comprises bone screws for insertion through the screw holes to attach the ratchet pieces to the associated bone segments, the bone screws made of a bio-absorbable material which takes at least as long to be absorbed by the patient as does the part of the ratcheting assembly which is made of bio-absorbable material.

23. The system of claim 12 wherein the ratcheting assembly is a reducer, and the first direction represents a decrease in the separation between the ratchet pieces, so as to facilitate consolidation of the bone segments.

24. The system of claim 12 wherein the ratcheting assembly is a distractor, and the first direction represents an increase in the separation between the ratchet pieces, so as to permit osteosynthesis in the bone repair region between the bone segments.

25. A method for treating a bone repair site in a patient comprising the steps of:

(a) subcutaneously implanting a first ratchet piece on the patient's bone on one side of the bone repair site;

(b) subcutaneously implanting a second ratchet piece on the patient's bone on the other side of the bone repair site;

(c) percutaneously inserting an adjustment assembly through an incision in the patient's skin, the incision being substantially smaller than the ratchet pieces, the adjustment assembly comprising a longitudinal axis, a first adjustment portion, and a second adjustment portion, wherein the first and second adjustment portions are slidingly engaged to permit controlled relative displacement along the longitudinal axis;

(d) releasably engaging the adjustment assembly with the first and second ratchet pieces;

(e) displacing the first and second adjustment portions relative to each other, so as to result in an incremental modification of the distance separating the first and second ratchet pieces;

(f) disengaging the adjustment assembly from the ratchet pieces;

(g) removing the adjustment assembly from the patient; and (h) repeating steps (c)–(g) as desired or necessary to treat the bone repair site.

26. The method of claim 25, further comprising the step of making at least one of the first or second ratcheting pieces at least in part of a bio-absorbable material.

27. The method of claim 26, wherein at least one of steps (a) or (b) comprises the steps of:

(i) providing a bone screw made of a bio-absorbable material which takes at least as long to be absorbed by the patient as does that part of the first or second ratcheting piece which is made of bio-absorbable material; and (ii) using the bone screw to attach the ratchet piece to the patient's bone.

* * * * *